United States Patent
Mohiuddin et al.

(10) Patent No.: US 11,450,412 B1
(45) Date of Patent: Sep. 20, 2022

(54) SYSTEM AND METHOD FOR SMART POOLING

(71) Applicant: Specialty Diagnostic (SDI) Laboratories, Inc., Garden Grove, CA (US)

(72) Inventors: Ozman Mohiuddin, Redmond, WA (US); William Henry Haase, Clarksville, TN (US); Yashashree Shende, Garden Grove, CA (US); Sumi Thomas, Rancho Santa Margarita, CA (US)

(73) Assignee: Specialty Diagnostic (SDI) Laboratories, Inc., Garden Grove, CA (US)

( * ) Notice: Subject to any disclaimer, the term of this patent is extended or adjusted under 35 U.S.C. 154(b) by 0 days.

(21) Appl. No.: 17/389,565

(22) Filed: Jul. 30, 2021

(51) Int. Cl.
*G16H 10/40* (2018.01)
*G16H 50/20* (2018.01)
*G06N 7/00* (2006.01)

(52) U.S. Cl.
CPC ............ *G16H 10/40* (2018.01); *G06N 7/005* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 6,566,052 | B1 | 5/2003 | Peddada et al. |
| 8,703,492 | B2 | 4/2014 | Self et al. |
| 10,043,054 | B2 | 8/2018 | Remiszewski et al. |
| 10,208,347 | B2 | 2/2019 | Seul et al. |
| 10,378,008 | B2 | 8/2019 | Roth et al. |
| 2003/0187592 | A1 | 10/2003 | Ohta et al. |
| 2017/0298436 | A1 | 10/2017 | Kaseniit et al. |

FOREIGN PATENT DOCUMENTS

| | | |
|---|---|---|
| WO | 2019155071 | 8/2019 |
| WO | 2020188471 | 9/2020 |
| WO | 2021011698 | 1/2021 |

OTHER PUBLICATIONS

Escobar et al. Smart Pooling: AI-powered COVID-19 testing medRxivpreprint doi: https://doi.org/10.1101/2020.07.13.20152983 (Year: 2020).*
Weinberg Editorial: Making the Best Use of Test Kits for COVID-19 American Journal of Epidemiology vol. 189, pp. 363-364 (Year: 2020).*
McMahan et al. Informative Dorfman Screening Biometrics vol. 68, pp. 287-296 (Year: 2012).*
Riley et al. High prevalence of SARS-CoV-2 swab positivity and increasing R number in England during Oct. 2020: REACT-1 round 6 interim report pp. 1-23 medRxiv https:doi.org/10.1101/2020.10.30.20223123 (Year: 2020).*
Mahase Covid-19: What is the R number? British Medical Journal 369:m1891 doi:10.1136/bmj.m1891 (Year: 2020).*
Escobar et al, Smart Pooling: AI-powered COVID-19 testing, Jul. 15, 2020.
Bilder et al, Pooled testing procedures for screening high volume clinical specimens in heterogeneous populations, Nov. 30, 2012.

\* cited by examiner

*Primary Examiner* — John S Brusca
(74) *Attorney, Agent, or Firm* — Caldwell Intellectual Property Law

(57) ABSTRACT

A system for smart pooling includes a computing device configured to obtain a feature datum, identify a predictive prevalence value as a function of the feature datum, wherein identifying the predictive prevalence value further comprises receiving a predictive training set correlating the feature datum with a probabilistic outcome, training a predictive machine-learning model as a function of the predictive training set, and identifying the predictive prevalence value as a function of the trained predictive machine-learning model and the feature datum, and determine an enhanced well count, wherein determining the enhanced well count further comprises generating a pooling threshold, and determining the enhanced well count as a function of the pooling threshold and the predictive prevalence value.

20 Claims, 9 Drawing Sheets

SYSTEM AND METHOD FOR SMART POOLING

FIELD OF THE INVENTION

The present invention generally relates to the field of laboratory sample testing. In particular, the present invention is directed to a system and method for smart pooling.

BACKGROUND

The need for fast patient results is the key to controlling infectious rates and maintaining them at a low level. Currently, the average turnaround time for a confirmatory testing for an illness is one day for priority patients and 3-5 days for other populations. In a climate where faster turnaround times would help to isolate those who test positive more quickly in order to prevent further spread, longer turnaround times make it difficult to predict potential "hot spots."

SUMMARY OF THE DISCLOSURE

In an aspect, a system for smart pooling includes a computing device configured to obtain a feature datum, identify a predictive prevalence value as a function of the feature datum, wherein identifying the predictive prevalence value further comprises receiving a predictive training set correlating the feature datum with a probabilistic outcome, training a predictive machine-learning model as a function of the predictive training set, and identifying the predictive prevalence value as a function of the trained predictive machine-learning model and the feature datum, and determine an enhanced well count, wherein determining the enhanced well count further comprises generating a pooling threshold, and determining the enhanced well count as a function of the pooling threshold and the predictive prevalence value.

In another aspect, a method for smart pooling includes obtaining, by a computing device, a feature datum, identifying, by the computing device, a predictive prevalence value as a function of the feature datum, wherein identifying the predictive prevalence value further comprises receiving a predictive training set correlating the feature datum with a probabilistic outcome, training a predictive machine-learning model as a function of the predictive training set, and identifying the predictive prevalence value as a function of the trained predictive machine-learning model and the feature datum, and determining, by the computing device, an enhanced well count, wherein determining the enhanced well count further comprises generating a pooling threshold, and determining the enhanced well count as a function of the pooling threshold and the predictive prevalence value.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for smart pooling. In an embodiment, this disclosure can be used to obtain a feature datum. Aspects of the present disclosure can be used to identify a predictive prevalence value. This is so, at least in part, because the disclosure utilizes a machine-learning model. Aspects of the present disclosure can also be used to determine an enhanced well count as a function of a pooling threshold. Aspects of the present disclosure allow for the practical application of reducing the amount of time for sample processing and analysis. Exemplary embodiments illustrating aspects of the present disclosure are described below in the context of several specific examples.

Figure 1:
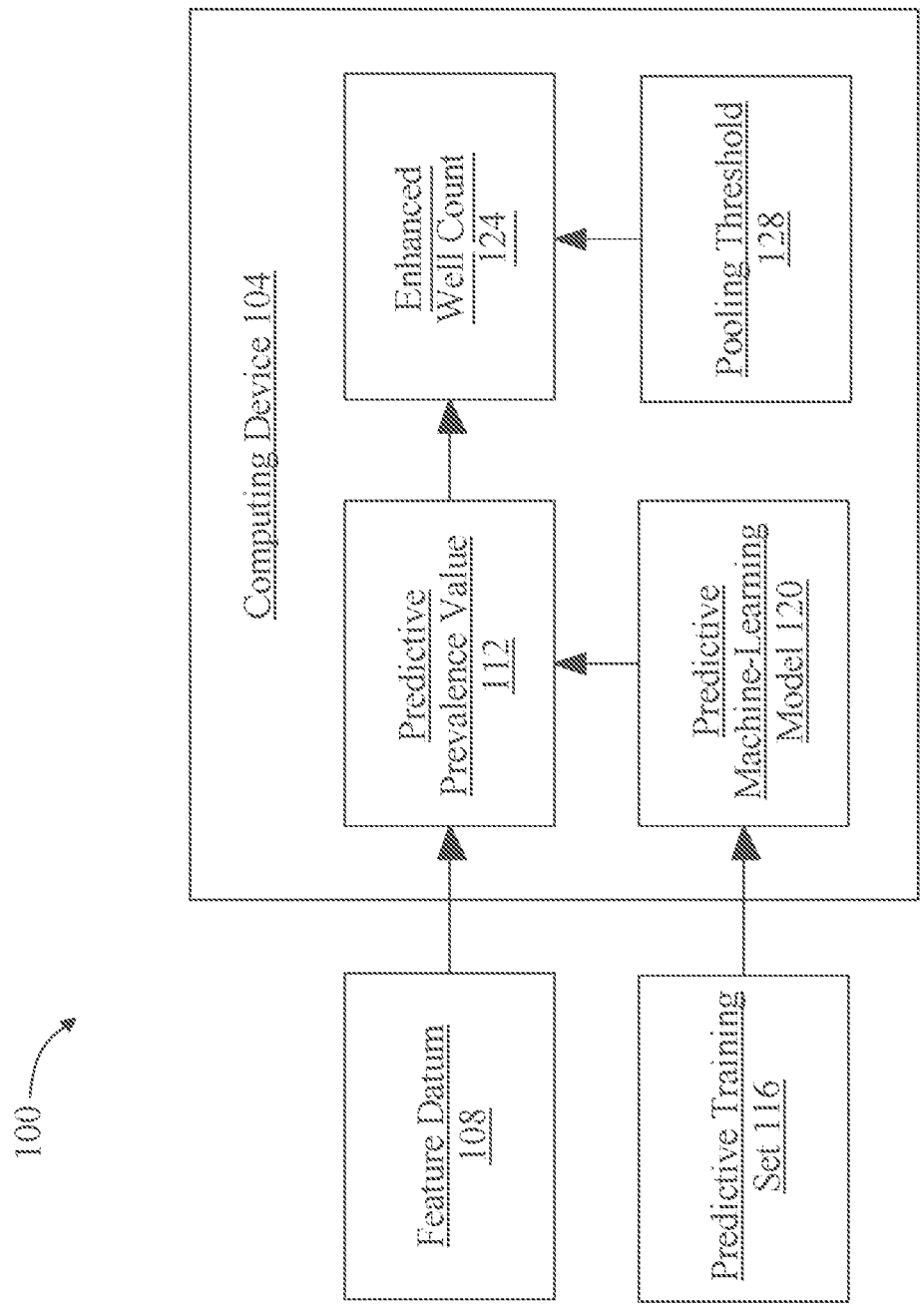
FIG. 1 is a block diagram illustrating an exemplary embodiment of a system for smart pooling.

Referring now to FIG. 1, an exemplary embodiment of a system 100 for smart pooling is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting Computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to obtain a feature datum 108. As used in this disclosure a "feature datum" is an element of data relating to a patient and/or individual. In an embodiment, feature datum 108 may denote one or more elements of data such as a patient's demographics, such as but not limited to age, weight, occupation, hobbies, and the like thereof. In an embodiment, and without limitation, feature datum 108 may denote a familial history. For example, and without limitation, a familial history may include one or more elements of datum denoting heritage, culture, ethnicity, and the like thereof. In an embodiment, and without limitation, feature datum 108 may denote a geolocation element. As used in this disclosure a "geolocation element" is an element of data representing regions and/or nationalities that a patient resides in and/or has resided in. For example, and without limitation, geolocation element may include an element of data representing one or more residential locations, residential histories, and the like thereof. In an embodiment, and without limitation, feature datum 108 may denote one or more medical records and/or medical histories. For example, and without limitation, feature datum 108 may include datum relating to HIPPA compliant patient intake datum including, but not limited to a patient's name, ethnicity, number of members of the patient's household, date of birth, and/or contact information such as but not limited to a cell phone number, email, mailing address, and the like thereof. In an embodiment, and without limitation, medical records and/or medical histories may denote one or more underlying medical conditions that a patient may have such as a previous infection and/or previous interaction with a virus and/or bacteria. For example, and without limitation, medical records may denote that a patient has previously contracted COVID-19 and/or received a vaccination for COVID-19. In an embodiment, and without limitation, medical records and/or medical histories may denote one or more medications that a patient is consuming and/or being treated with. For example, and without limitation, one or more medications may include prescription medications such as but not limited to oseltamivir, zanamivir, peramivir, baloxavir marboxil, remdesivir, and the like thereof. In another embodiment, and without limitation, one or more medications may include non-prescription medications such as but not limited to, supplements, vitamins, minerals, and over the counter medications, and the like thereof.

In an embodiment, and still referring to FIG. 1, computing device 104 may obtain feature datum 108 as a function of identifying a clinical element. As used in this disclosure a "clinical element" is an element of data representing an individual's biological system. In an embodiment, and without limitation, clinical element may denote a health status of the individual, wherein a health status is a measure of the relative level of physical, social and/or behavioral well-being. In another embodiment, clinical element may denote one or more health statuses of an individual's nervous system, circulatory system, musculoskeletal system, respiratory system, endocrine system, integumentary system, lymphatic system, digestive system, urinary system, reproductive system, and the like thereof. For example, and without limitation, clinical element may include one or more medical representations of a patient, such as a lab specimen. In an embodiment, and without limitation, computing device 104 may be configured to receive a lab specimen associated with the feature datum. As used in this disclosure a "lab specimen" is one or more biological extractions collected from an individual. Lab specimen may include, without limitation, exhalate, blood, sputum, urine, saliva, feces, semen, tissues, organs, saliva, DNA/RNA, hair, nail clippings, or any other cell or fluids. Lab specimen may include one or more biomarkers. As used in this disclosure a "biomarker" is a molecule and/or chemical that identifies the status of an individual's health system and/or stress of an individual's health system. As a non-limiting example, biomarkers may include leukocytes, neutrophils, PCT, ferritin, interleukin-2R, interleukin-6, interleukin-8, interleukin-10, tumor necrosis factor, anti-inflammatory cytokines, c-reactive protein, metal ions, NADPH, P450, ascorbic acid, vitamin E, and the like thereof. In an embodiment, and without limitation, lab specimen may contain viral proteins and/or genetic material (including without limitation ribonucleic acid (RNA) and/or deoxyribonucleic acid (DNA)), and/or other proteins associated with disease agents, where disease agents may include pathogens such as bacteria, archaea, protists, fungi, infections proteins such as prions, parasitic multicellular organisms such as nematodes including without limitation ascarids and/or filarial worms, flatworms including without limitation flukes and tapeworms, insectoid parasites such as without limitation botflies and/or screw worms, or the like, potentially indicative of an infection. Lab specimen may come from either an adult or a child. Lab specimen may be collected according to established protocols depending on the origin of the specimen. For example, collection of a lab specimen from the upper respiratory tract may use a nasopharyngeal swab method. Other examples of upper respiratory tract collection methods include, but are not limited to, a nasal mid-turbinate (NMT) swab and the nasopharyngeal wash, and/or the nasal wash/aspirate method. A lower respiratory tract sample may include the collection of sputum. Collection of a lab specimen from the throat region may involve the use of the oropharyngeal swab method. Other methods of collection, including without limitation extraction of fluids, tissue samples, biopsies, or the like may be employed to collect specimen.

Further referring to FIG. 1, lab specimen may be collected from a third-party provider. Examples of third-party providers include nursing homes, a hospital, a drive-through site, a pharmacy, a healthcare professional's office, an urgent care facility, and the like. Lab specimen may be preserved by refrigeration with ice or by snap freezing the sample in a dry ice/ethanol slurry. Specimens may be shipped for analysis using services such as the United States Postal Service, or private couriers such as Federal Express, United Parcel Service, or the like. A "disease agent" as defined in this disclosure, is any organism that causes disease, such as bacteria, virus, fungus, or protozoa. Disease agents may be transmitted by, for example, skin contact, bodily fluids, airborne particles, contact with bodily fluids, and by contact with a surface originally touched by an infected person. Examples of first disease agents include, but are not limited to Anthrax, Aspergillosis, Blastomycosis, Chicken pox, Adenovirus, Enterovirus, Rotavirus, Influenza, Coronaviridae such as, SARS-CoV-2 or any coronavirus, *Clostridium botulinum, Yersinia Pestis, Escherichia coli*, any other disease agent described in this disclosure, and the like. Lab specimen may include genetic material collected from a human subject using a collection device and stored in a collection carrier. As used in this disclosure, "genetic material" is material used to store genetic information in the nuclei or mitochondria or an organism's cell. Genetic material may include DNA and/or ribonucleic acid RNA. A potential infection may occur, for example, when a viral disease agent attaches to a specific host cell. Viral genetic information may then be inserted into a host cell where it starts to replicate, transcribe DNA into messenger RNA (mRNA) and translate mRNA into a viral protein. A new viral complex may then be released from the cell.

Still referring to FIG. 1, in an embodiment, collection device may include a swab and/or a transfer medium where the swab may be dipped in the transfer medium. Collection site to be used for testing may affect a type of swab used. Types of swabs that may be used include, but are not limited to, synthetic fiber swabs with plastic shafts such as COPAN FLOSwabs® 501CS01 for use in a nasopharyngeal site, a foam swab which may be used in nasal collection, and the like. Synthetic fibers used in swabs may include spun polyester fiber, spun rayon fiber, and the like. Swabs may be included as part of a disease agent testing kit. For example, a disease agent testing kit may include at least a swab, a sterile vessel that serves as a transport device, a transfer medium, a diagnostic requisition form, instructions, a unique identifier, and a bag for use to ship the sample to the testing laboratory. Sterile vessel may include without limitation a glass vial with a stopper, a plastic urine sample cup, a test tube, or the like. Transfer medium may include a buffer. The buffer may include a lysis buffer. As used in this disclosure, a "lysis" buffer is a buffer used for its ability to break up cells. Examples of a lysis buffer include, without limitation, an NP-40 lysis buffer, a sodium dodecyl sulfate (SDS) lysis buffer, an ammonium-chloride-potassium (ACK) lysing buffer, and the like. Transfer medium may be stable for a period ranging from at least 5 to 7 days. In a non-limiting example, a sample may be collected from a human subject by inserting a spun polyester swab with a plastic shaft into the nasopharyngeal cavity of a human subject. Post-sampling activities may include breaking plastic shaft in order to fit a sample into a sterile vessel which contains transfer medium. Swab may be dipped into transfer medium contained in transfer vessel. Transfer vessel may be sealed, and a unique identifier placed on sample, for instance in the form of a label, which may be alphanumeric and/or a machine-readable label such as without limitation a bar code and/or quick-read (QR) code. Sample and one or more diagnostic requisition forms may be placed in a bag; the bag may be shipped to a testing lab.

Alternatively or additionally, and with continued reference to FIG. 1, collection device may include blotting paper. As defined in the disclosure, "blotting paper" is paper that can be used for collection of biological materials. A non-limiting example of material that can be collected using blotting paper includes blood. An example of paper that can be used as blotting paper includes filter paper. Filter paper may be made from high purity cotton linters. As an example, to analyze for presence or absence of antibodies for the influenza A infection, a dried blood specimen is collected by applying drops of a human subject's blood onto the blotting paper. Blood may be drawn by lancet from a finger, heel, toe, or the like. Once blood dries on paper, it may be shipped to a lab with a diagnostic requisition form and/or a unique identifier for analysis.

Alternatively or additionally, and further referring to FIG. 1, collection device may include a sterile dry container. Dry container may include any closure device to close dry container. These may include, but are not limited to, threaded closures, stoppers, metal caps, and the like. Collection device may contain sputum. As an example, a human subject may expectorate a sample of sputum into a dry container; once collected, the dry container containing the sputum may be shipped to a lab with a diagnostic requisition form and/or a unique identifier for analysis.

Still referring to FIG. 1, specimen may also include a unique identifier associated to lab specimen. As defined in this disclosure, a "unique identifier" is any identifier that refers to only one human subject. A unique identifier may include a specific sequence of characters, numbers, letters, and/or words that may identify a particular human subject. A unique identifier may include a globally recognized uniform identifier such as a uniform code commission (UCC) barcode. A unique identifier may include an optically captured and/or an otherwise captured identifier from a near field communication (NFC) tag or a radio frequency identifier (RFID) tag. As an example, a barcode containing human subject descriptive data may be included in the disease agent sampling kit which is used to acquire the specimen. As defined in this specification, "human subject descriptive data" is defined as data that is unique to a particular human subject. Human subject descriptive data may include, but without limitation, a subject's name, contact information, ethnicity, number of people residing in the subject's household, and the like. Human subject descriptive data may further include, without limitation, the subject's symptoms, the subject's data of birth, any recent infections, any locations where the subject has travelled to, any known exposure to disease agents, medications, allergies, and the like.

In an embodiment, and still referring to FIG. 1, clinical element may be obtained as a function of an instrument. As used in this disclosure an "instrument" is a device and/or tool capable of recording and/or ascertaining a measurement associated with a sample. In an embodiment, instrument may include one or more devices that collect, store, and/or calculate one or more lights, voltages, currents, sounds, chemicals, pressures, and the like thereof that are associated with the individual's health status. For example, and without limitation instrument may include a magnetic resonance imaging device, magnetic resonance spectroscopy device, x-ray spectroscopy device, computerized tomography device, mass spectrometer, ultrasound device, electroretinogram device, electrocardiogram device, ABER sensor, and the like thereof. In an embodiment, instrument may include a liquid chromatography mass spectrometer. As used in this disclosure a "liquid chromatography mass spectrometer" is an analytical instrument that combines a physical separation with a mass analyzer. In an embodiment, and without limitation, liquid chromatography mass spectrometry may include a physical separation component. As used in this disclosure a "physical separation component" is a component capable of separating analytes and/or lab specimens. In an embodiment, and without limitation, physical separation component may include a component that separates analytes as a function of a stationary phase and a mobile phase. For example, and without limitation, a stationary phase may include a phase comprising a porous solid such as but not limited to glass, silica, alumina, free silanol, bonded silanol, geminol silanol, siloxane, and the like thereof. As a further non-limiting example, a mobile phase may include a phase comprising a liquid solvent such as but not limited to water, acetonitrile, chloroform, isopropyl alcohol, ethanol, hexane, butane, propane, benzene, and the like thereof. In an embodiment and without limitation, physical separation component may separate analytes and/or lab specimens as a function of a capacity factor, k'. As used in this disclosure a "capacity factor" is a measurable value representing the strength of the interaction of the analyte and/or lab specimen with the stationary phase as it flows through the mobile phase, wherein the capacity factor is determined by:

$$k' = \frac{t_r - t_m}{t_m}$$

where $t_r$, is the retention time of the analyte and $t_m$, is the retention time of a reference compound, wherein a "reference compound," as used herein, is a compound that has a known retention time and/or does not interact with the stationary phase. As used in this disclosure a "retention time" is a time period that it takes for a compound to travel through the physical separation component, wherein a time period includes a distance of time expired such as seconds, minutes, hours, days, and the like thereof. In an embodiment, and without limitation, physical separation component may separate analytes and/or lab specimens as a function of a selectivity factor, α. As used in this disclosure a "selectivity factor" is a measurable value associated with the amount of separation between two or more analytes and/or lab specimens, wherein selectivity factor is determined by:

$$\alpha = \frac{k'_2}{k'_1} = \frac{t_{r_2} - t_m}{t_{r_1} - t_m}$$

where, $t_{r_1}$ is the retention time of a first analyte, $t_{r_2}$, is the retention time of a second analyte, $k'_1$, is the capacity factor of the first analyte, and $k'_2$, is the capacity factor of the second analyte. For example, and without limitation, the selectivity factor for physical separation component may be 2.15 for the amount of separation between interleukin-6 and c-reactive protein dissolved in an acetonitrile mobile phase and interacting with a geminal silanol stationary phase.

Still referring to FIG. 1, liquid chromatography mass spectrometer may include a mass analyzer component. As used in this disclosure a "mass analyzer component" is a component capable of analyze a mass to charge ratio and/or ion of an analyte and/or lab specimen. In an embodiment, and without limitation, mass analyzer component may include a linear quadrupole. As used in this disclosure a "linear quadrupole" is a mass analyzer that filters ions as a function of four metal rods that create a quadrupolar electric field. The quadrupolar electric field may allow ions of specific mass to charge ratios to be guided along the central axis of the four parallel arranged rods, while eliminating other mass to charge ratios. In an embodiment, and without limitation, the four metal rods may be hyperbolic which may match the electric field that is produced. In an embodiment, and without limitation, the quadrupolar electric field may be generated by the four rods through a series of tunable RF and DC voltages. In an embodiment, and without limitation, linear quadrupole may allow for specific mass to charge ratios to be selected and/or a range of mass to charge ratios to be selected to allow for either an entire mass window to be collected and/or peak hopping, wherein "peak hopping," is the analysis of a specific peak and/or mass to charge ratio to be identified. In another embodiment, and without limitation, mass analyzer component may include a time-of-flight mass analyzer. As used in this disclosure a "time-of-flight mass analyzer" is a mass analyzer that separates ions over time across a field-free drift space. As used in this disclosure a "field-free drift space" is an enclosed space wherein a limited and/or no electric field interacts with the ions present in the enclosed space. In an embodiment, and without limitation, ions may be focused into an ion packet. As used in this disclosure an "ion packet" is a group and/or cluster of ions. Ion packet may be pulsed into the field-free drift space with a uniform amount of kinetic energy. The uniform kinetic energy provided to the ion packet may allow the smaller ions to have higher kinetic velocities compared to the larger ions, wherein the smaller ions will reach the detector faster, due to the higher velocity, while the larger ions will reach the detector slower, due to the lower velocity. In an embodiment, and without limitation, mass analyzer component may include a tandem mass spectrometer component. As used in this disclosure a "tandem mass spectrometer component" is a component capable of elucidating structural data of an ion and/or mass to charge ratio. For example, and without limitation, tandem mass spectrometer component may fragment one or more ions of interest to produce a fragmented charged ion and a neutral loss. As used in this disclosure a "fragmented charged ion" is an ion that lacks at least an atom of the parent ion, wherein a parent ion is the first ion present in the mass analyzer component. For example, and without limitation, fragmented charged ion may include a daughter ion and/or ion having a direct relationship to the parent ion. As used in this disclosure a "neutral loss" is a neutral analyte and/or atom that is expelled from the parent ion. In an embodiment, and without limitation, tandem mass spectrometer component may elucidate structural data as a function of an ion activation method such as but not limited to collision-induced dissociated, surface induced dissociation, electron transfer dissociation, in-source decay, post-source decay, photodissociation, and the like thereof.

Still referring to FIG. 1, an instrument may include a polymerase chain reaction component. As used in this disclosure a "polymerase chain reaction component" is an instrument that amplifies deoxyribonucleic acid (DNA) samples. In an embodiment, and without limitation, polymerase chain reaction component may amplify a small quantity of DNA sample to a large quantity such that an analysis may be performed. In another embodiment, and without limitation, polymerase chain reaction component may include a thermal cycling element. As used in this disclosure a "thermal cycling component" is a component that exposes a first chemical to repeated cycles of heating and cooling. In an embodiment, and without limitation, thermal cycling component may allow for DNA melting, enzyme-driven DNA replication, and the like thereof. In an embodiment, and without limitation, polymerase chain reaction component may include a primer. As used in this disclosure a "primer" is a single-stranded nucleic acid used by living organisms in the initiation of DNA synthesis. In an embodiment, and without limitation, primer may include an oligonucleotide that is a complementary sequence to a target DNA region. Additionally or alternatively, polymerase chain reaction component may include a DNA polymerase. As used int this disclosure a "DNA polymerase" is an enzyme that catalyzes the synthesis of DNA molecules from molecular precursors of DNA. In an embodiment, and without limitation, DNA polymerase may create two identical DNA duplexes from a single original DNA duplex. In another embodiment and without limitation, DNA polymerase may a nucleotides to a three prime (3')-end of a DNA strand. In an embodiment, and without limitation, DNA polymerase may include a heat-stable DNA polymerase. As used in this disclosure a "heat-stable DNA polymerase" is an enzyme capable of catalyzing DNA synthesis at high temperatures. For example, and without limitation, heat-stable DNA polymerase may include a Taq polymerase enzyme. In an embodiment and without limitation, polymerase chain reaction component may be configured to perform DNA cloning, gene cloning, gene manipulation, gene mutagenesis, construction of DNA-based phylogenies, diagnosis of genetic disorders, monitoring of genetic disorders, amplification of DNA, analysis of DNA genetic fingerprints, detection of pathogens in nucleic acid tests, and the like thereof. Additionally or alternative and without limitation, polymerase chain reaction component may include any polymerase chain reaction instrument as described in U.S. Nonprovisional application Ser. No. 16/990,366, filed on Aug. 11, 2020, and entitled "A METHOD AND SYSTEM FOR CLASSIFYING SAMPLE DATA FOR ROBOTICALLY EXTRACTED SAMPLES," the entirety of which is incorporated herein by reference.

In an embodiment and still referring to FIG. 1, polymerase chain reaction component may include a quantitative Polymerase Chain Reaction (qPCR) instrument and/or a real time PCR instrument with thermal control. For example, and without limitation, real time PCR instruments may include the LightCycler96 (Catalog No. 05815916001, Roche) or Thermo Fisher Scientific QuanStudio 5 Series qPCR system with 384 well plate capacity (Catalog No. A28140). In an embodiment, and without limitation, as PCR progress is monitored by fluorescence, the real time PCR instrument may include a fluorimeter. As an example, RNA is converted to complementary DNA by reverse transcription. The PCR reaction amplifies and detects the sequence of interest which uses fluorescence reporters as a real time detection mechanism. Following the amplification of complementary DNA after a number of cycles, a sequence of interest, for example, for a disease agent of interest may be measured. For example, after 45 PCR cycles, the human subject specimen may generate a complementary DNA sequence that shows the presence of the SARS-CoV-2 viral DNA. This may indicate a positive result for the presence of the virus. In an embodiment, the test result is a positive result. In another embodiment, communications with an authorized human subject contact may be established as a function of the positive test result.

Still referring to FIG. 1, an instrument may include a flow cytometer. As used in this disclosure a "flow cytometer" is an instrument capable of detecting and/or measuring physical and/or chemical characteristics of a population of cells and/or particles. In an embodiment, and without limitation, flow cytometer may be configured to include a flow cell. As used in this disclosure a "flow cell" is a narrow hollow tube that orients the sample to travel along the tube in an orderly manner. For example, and without limitation, flow cell may include a tube and/or sheath that carries and aligns cells and/or lab specimens to travel through the tube. In an embodiment and without limitation flow cell may include a tube that orients the cell and/or lab specimen such that only one cell and/or lab specimen interacts with a measuring device. As used in this disclosure a "measuring device" is a device and/or component that detect light signals as a function of the cell and/or lab specimen. In an embodiment, and without limitation, measuring device may include one or more optical devices. In an embodiment, and without limitation, optical devices may include lamps such as but not limited to, mercury lamps, xenon lamps, halogen lamps, and the like thereof. In another embodiment, and without limitation, optical devices may include high-power water-cooled lasers such as but not limited to, argon lasers, krypton lasers, dye lasers, and the like thereof. In another embodiment, and without limitation, optical devices may include low-power air-cooled lasers such as but not limited to, argon lasers, red-HeNe lasers, green-HeNe lasers, HeCd lasers, diode lasers, and the like thereof. In an embodiment, and without limitation, measurement device may transmit the signal to a detector. As used in this disclosure a "detector" is a component and/or device that detects analog measurements. In an embodiment, and without limitation detector may detect one or more analog measurements such as forward-scattered light measurements, side-scattered light measurements, dye-specific fluorescence signals, and the like thereof. In an embodiment, and without limitation, flow cytometer may include an amplification system. As used in this disclosure an "amplification system" is a system that amplifies and/or converts a digital signal to enhance the signal such that computing device 104 may receive a voltage. For example, and without limitation, amplification system may include an analog-to-digital converter. As a further non-limiting example, amplification system may amplify the signal as a function of a linear and/or logarithmic amplification process.

Still referring to FIG. 1, clinical element may include an element of data from a serological test on a blood sample to detect the presence of antibodies for a disease agent. For example, the analysis may look for antibodies against a disease agent like the SARS-CoV-2 virus for infections that have occurred in the past. A serological test may be performed using an enzyme-linked immunosorbent assay or ELISA-based test. An ELISA assay uses a solid-phase type of enzyme immunoassay (EIA) to detect the presence of a protein in a liquid sample using antibodies directed against the protein to be measured. Detection may be accomplished by measuring the activity of the reporter enzyme via incubation with the appropriate substrate to produce a measurable product. ELISA-based serological testing protocols for viruses, such as but not limited to, SARS-CoV-2 have been established by the Center for Disease Control (see, for example, "Serology Testing for COVID-19 at CDC").

Still referring to FIG. 1, obtaining feature datum 108 may further comprise receiving a medical input. As used in this disclosure a "medical input" is an element of data that is obtained relating to an individual's health system. As a non-limiting example, medical input may include an informed advisor that enters a medical assessment comprising a physical exam, neurologic exam, blood test, urine test, imaging test, cellular and/or chemical analysis, genetic test, measurement, visual examination, and the like thereof. As a further non-limiting example, medical input may include one or more questionnaires and/or surveys that identify one or more medical records, medical evaluations, and the like thereof. As a further non-limiting example, medical input may include one or more inputs from a family member. For example, and without limitation, a brother, sister, mother, father, cousin, aunt, uncle, grandparent, child, friend, and the like thereof may enter an individual's medical records relating to the health system of the patient.

Still referring to FIG. 1, computing device 104 identifies a predictive prevalence value 112 As used in this disclosure a "predictive prevalence value" is a measurable value representing a prevalence of an infection and/or viral disease as a function of feature datum 108, wherein a "prevalence," as used herein, is a proportion of a particular population found to be affected by a medical condition at a specific time. For example, and without limitation, predictive prevalence value 112 may denote a prevalence as a function of a feature datum 108 of a plurality of feature data. As a further non-limiting example, predictive prevalence value 112 may denote a prevalence of an infectious disease such as influenza as a function of feature data such as medical history, hobbies, occupation, and the like thereof. In another embodiment, and without limitation, predictive prevalence value 112 may be a value of 0.4 for a disease of malaria. In another embodiment, and without limitation, predictive prevalence value 112 may be a value of 0.85 for a risk factor such as, but not limited to smoking, seat-belt use, and the like thereof. As a further non-limiting example, predictive prevalence value may be 0.92 for COVID-19.

In an embodiment, and still referring to FIG. 1, predictive prevalence value 112 is identified as a function of receiving a predictive training set 116. As used in this disclosure a "predictive training set" is a training set that correlates a feature datum and a probabilistic outcome to a predictive prevalence value. As used in this disclosure a "probabilistic outcome" is an outcome that exceeds a threshold value, expressed on [0,1], wherein exceeding the threshold denotes a likelihood of the outcome occurring. For example, and without limitation, probabilistic outcome may denote that a threshold relating to a contagion factor has been exceeded such that there is a high probability for a positive result for West Nile Virus infection. As used in this disclosure a "contagion factor" is a quantitative value denoting the contagiousness of a viral agent and/or bacteria. In an embodiment and without limitation, contagion factor may include a basic reproduction number, $R_0$. As used in this disclosure a "basic reproduction number" is the expected number of cases directly generated by one case in a population where all individuals are susceptible to infection. For example, and without limitation, Ebola may have a $R_0$ of 1.5-1.9. As a further non-limiting example, HIV/AIDS may have an $R_0$ of 2-5. For example, and without limitation a contagion factor may be less than 1, wherein a value less than 1 denotes that each infected individual may infect less than one new individual. As a further non-limiting example, a contagion factor may equal to 1, wherein a value of 1 denotes that each infected individual may infect one new individual. As a further non-limiting example, a contagion factor may greater than 1, wherein a value greater than 1 denotes that each infected individual may infect more than one new individual. In an embodiment, and without limitation, probabilistic outcome may denote that a threshold relating to a contagion factor has not been exceeded as a function of a herd immunity element. For example, and without limitation, probabilistic outcome may denote that a threshold value for a contagion factor was not exceeded due to a herd immunity element, wherein the lack of exceeding the threshold value may denote a negative result for COVID-19 infection.

In an embodiment, and still referring to FIG. 1, predictive training set 116 may include relating a feature datum associated with a weak immune system and a probabilistic outcome of a high probability for contracting mononucleosis to a predictive prevalence value of 0.45. In an embodiment, and without limitation, predictive training set 116 may be received as a function of user-entered valuations of feature data, probabilistic outcomes, and/or predictive prevalence values. Computing device 104 may receive predictive training set 116 by receiving correlations of feature data, and/or probabilistic outcomes that were previously received and/or identified during a previous iteration of identifying predictive prevalence values. Predictive training set 116 may be received by one or more remote devices that at least correlate a feature datum and/or probabilistic outcome to a predictive prevalence value. As used in this disclosure "remote device" is an external device to computing device 104. The predictive training set may be received in the form of one or more user-entered correlations of a feature datum and/or probabilistic outcome to a predictive prevalence value. Additionally or alternatively, a user may include an informed advisor, wherein an informed advisor may include, without limitation, psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may train a predictive machine-learning model 120 as a function of predictive training set 116. As used in this disclosure "predictive machine-learning model" is a machine-learning model to produce a predictive prevalence value output given feature data as inputs; this is in contrast to a non-machine learning software program where the commands to be executed are determined in advance by a user and written in a programming language. Predictive machine-learning model 120 may include one or more predictive machine-learning processes such as supervised, unsupervised, or reinforcement machine-learning processes that computing device 104 and/or a remote device may or may not use in the determination of predictive prevalence value 112, wherein a remote device is described above in detail. Predictive machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof. In an embodiment, and without limitation, predictive machine-learning model 120 may identify a predictive prevalence value of 0.88 as a function of a feature data associated with an exposure to varicella for 3 days, a previous medical record of never having varicella, and a high probability of testing positive as a function of a contagion factor of 11, wherein predictive machine-learning model 120 performed a binomial logistic regression.

In an embodiment, and still referring to FIG. 1, computing device 104 may receive predictive machine-learning model 120 from a remote device that utilizes one or more predictive machine learning processes, wherein a remote device is described above in detail. For example, and without limitation, a remote device may include a computing device, external device, processor, and the like thereof. Remote device may perform the predictive machine-learning process using predictive training set 116 to generate predictive prevalence value 112 and transmit the output to computing device 104. Remote device may transmit a signal, bit, datum, or parameter to computing device 104 that at least relates to predictive prevalence value 112. Additionally or alternatively, the remote device may provide an updated machine-learning model. For example, and without limitation, an updated machine-learning model may be comprised of a firmware update, a software update, a predictive machine-learning process correction, and the like thereof. As a non-limiting example a software update may incorporate a new feature datum that relates to a modified predictive prevalence value. Additionally or alternatively, the updated machine learning model may be transmitted to the remote device, wherein the remote device may replace the predictive machine-learning model with the updated machine-learning model and determine the predictive prevalence value as a function of the feature datum using the updated machine-learning model. The updated machine-learning model may be transmitted by the remote device and received by computing device 104 as a software update, firmware update, or corrected predictive machine-learning model. For example, and without limitation predictive machine-learning model 120 may utilize a random forest machine-learning process, wherein the updated machine-learning model may incorporate a gradient boosting machine-learning process Additionally or alternatively, computing device 104 may identify predictive prevalence value 112 as a function of determining a probabilistic distribution. As used in this disclosure a "probabilistic distribution" is a range of probabilities of occurrence of different possible outcomes. In an embodiment, and without limitation probabilistic distribution may denote the likelihood of a probability occurring as a function of a range of potential possible outcomes that exist in an interval of [0,1], as described below in detail in reference to FIG. 5.

Still referring to FIG. 1, computing device 104 may determine predictive prevalence value 112 as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 determines an enhanced well count 124. As used in this disclosure an "enhanced well count" is an optimized number of analytes and/or lab specimens to be grouped prior to analysis. For example, and without limitation, enhanced well count 124 may denote that three analytes and/or lab specimens should be grouped together in a well for a PCR analysis. As a further non-limiting example, enhanced well count 124 may denote that twenty analytes and/or lab specimens should be grouped together in a well for a PCR analysis. As a further non-limiting example, enhanced well count 124 may denote that five analytes and/or lab specimens should be grouped together prior to performing a liquid chromatography mass spectrometric analysis. Computing device 104 determines enhanced well count 124 as a function of generating a pooling threshold 128. As used in this disclosure a "pooling threshold" is a threshold that denotes that an analyte and/or lab specimen should no longer be grouped together. For example, and without limitation, pooling threshold 128 may denote that no more than 3 lab specimens and/or analytes should be pooled and/or grouped together prior to analysis. In an embodiment, and without limitation, pooling threshold 128 may be generated as a function of receiving a probability limiter. In an embodiment, and without limitation, pooling threshold 128 may be inversely related to predictive prevalence value 112, wherein as predictive prevalence value 112 increases pooling threshold 128 may decrease, which may reduce the number of lab specimens that may be grouped prior to analysis. As used in this disclosure a "probability limiter" is a maximum amount of predictive prevalence value that may occur for a positive result before there is a limit at which no lab specimens may be pooled and/or grouped together. For example, and without limitation, probability limiter may denote that a predictive prevalence value may not exceed a value of 0.2 for grouping and/or pooling two or more lab specimens. As a further non-limiting example, probability limiter may denote that a predictive prevalence value may not exceed 0.37 for grouping and/or pooling of five or more m lab specimens.

Still referring to FIG. 1, computing device 104 may determine enhanced well count 124 as a function of generating an objection function to score and weight factors to achieve a well count score for each grouping. In some embodiments, groupings may be scored in a matrix for optimization, where columns represent predictive prevalence value and rows represent pooling thresholds potentially paired therewith; each cell of such a matrix may represent a score of a grouping of the corresponding enhanced well count.

With continued reference to FIG. 1, computing device 104 may determine enhanced well count 124 as a function of optimizing the objective function by performing a greedy algorithm process. A "greedy algorithm" is defined as an algorithm that selects locally optimal choices, which may or may not generate a globally optimal solution. For instance, computing device 104 may select groupings so that scores associated therewith are the best score for each predictive prevalence value and/or for each pooling threshold. In such an example, optimization may determine the enhanced well count such that each well includes the highest score possible.

Still referring to FIG. 1, objective function may be formulated as a linear objective function. Which computing device 104 may solve using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs}x_{rs}$, where R is the set of all predictive prevalence values r, S is a set of all pooling thresholds s, $c_{rs}$ is a score of a grouping of a given predictive prevalence value with a given pooling threshold, and $x_{rs}$ is 1 if a predictive prevalence value r is grouped with a pooling threshold s, and 0 otherwise. Continuing the example, constraints may specify that each predictive prevalence value is assigned to only one pooling threshold, and each pooling threshold is assigned only one predictive prevalence value. Sets of predictive prevalence values may be optimized for a maximum score combination of all generated predictive prevalence values. In various embodiments, system 100 may determine combination of predictive prevalence values that maximizes a total score subject to a constraint that all predictive prevalence values are paired to exactly one pooling threshold. A mathematical solver may be implemented to solve for the set of feasible groupings that maximizes the sum of scores across all groupings; mathematical solver may implemented on computing device 104 and/or another device in system 100, and/or may be implemented on third-party solver.

With continued reference to FIG. 1, optimizing objective function may include minimizing a loss function, where a "loss function" is an expression an output of which an optimization algorithm minimizes to generate an optimal result. As a non-limiting example, computing device 104 may assign variables relating to a set of parameters, which may correspond to score components as described above, calculate an output of mathematical expression using the variables, and select a grouping that produces an output having the lowest size, according to a given definition of "size," of the set of outputs representing each predictive prevalence value; size may, for instance, included absolute value, numerical size, or the like. Selection of different loss functions may result in identification of different potential groupings as generating minimal outputs. Objectives represented in an objective function and/or loss function may include maximizing the number of lab specimens to a well and/or maximizing well counts.

In an embodiment, and still referring to FIG. 1, computing device 104 may generate an assignment of lab specimen to a well as a function of enhanced well count 124. As used in this disclosure an "assignment" is direction and/or command for a plurality of lab specimens to be compiled into a group. For example, and without limitation, computing device 104 may generate an assignment such that a lab specimen is compiled into the well labeled "A4". As a further non-limiting example, computing device 104 may generate an assignment such that a lab specimen is compiled into the well labeled "G2". Computing device 104 generate the assignment of the lab specimen to enhanced well count 124 as a function of receiving a grouping element. As used in this disclosure a "grouping element" is an element of data denoting a similar feature datum. For example, and without limitation, grouping element may denote a plurality of lab specimens share a similar feature datum associated with an occupation and/or employment location. As a further non-limiting example, grouping element may denote a plurality of lab specimens share a similar feature datum associated with a demographic of an age range of 30-32 years old. In an embodiment, and without limitation computing device 104 may assign lab specimen as a function of grouping element and a grouping machine-learning model. As used in this disclosure a "grouping machine-learning model" is a machine-learning model to produce an assignment output given grouping elements as inputs; this is in contrast to a non-machine learning software program where the commands to be executed are determined in advance by a user and written in a programming language. Grouping machine-learning model may include one or more grouping machine-learning processes such as supervised, unsupervised, or reinforcement machine-learning processes that computing device 104 and/or a remote device may or may not use in the determination of assignment. A grouping machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train grouping machine-learning process as a function of a grouping training set. As used in this disclosure "grouping training set" is a training set that correlates a grouping element to an assignment. As a non-limiting example a grouping element of similar medical records may correlate to an assignment of a specific well and/or sample group. The grouping training set may be received as a function of user-entered valuations of grouping elements and/or assignments. Computing device 104 may receive grouping training by receiving correlations of grouping elements and/or assignments that were previously received and/or determined during a previous iteration of generating an assignment. The grouping training set may be received by one or more remote devices that at least correlate grouping elements to assignments, wherein a remote device is an external device to computing device 104, as described above. The grouping training set may be received by one or more user-entered correlations of grouping elements and/or feature datum to assignments.

Still referring to FIG. 1, computing device 104 may receive grouping machine-learning model from a remote device that utilizes one or more grouping machine learning processes, wherein a remote device is described above in detail. For example, and without limitation, a remote device may include a computing device, external device, processor, and the like thereof. Remote device may perform the grouping machine-learning process using the grouping training set to generate assignment and transmit the output to computing device 104. Remote device may transmit a signal, bit, datum, or parameter to computing device 104 that at least relates to assignments. Additionally or alternatively, the remote device may provide an updated machine-learning model. For example, and without limitation, an updated machine-learning model may be comprised of a firmware update, a software update, a grouping machine-learning process correction, and the like thereof. As a non-limiting example a software update may incorporate a new assignment that relates to a modified grouping element. Additionally or alternatively, the updated machine learning model may be transmitted to the remote device, wherein the remote device may replace the grouping machine-learning model with the updated machine-learning model and determine the assignment as a function of the grouping element using the updated machine-learning model. The updated machine-learning model may be transmitted by the remote device and received by computing device 104 as a software update, firmware update, or corrected grouping machine-learning model. For example, and without limitation grouping machine-learning model may utilize a neural net machine-learning process, wherein the updated machine-learning model may incorporate hierarchical clustering machine-learning process. In an embodiment, and without limitation, grouping machine-learning model may identify assignment as a function of one or more classifiers, wherein a classifier is described above in detail.

In an embodiment, and still referring to FIG. 1, computing device 104 may generate assignment as a function of identifying a similar predictive prevalence. As used in this disclosure a "similar predictive prevalence" is a first predictive prevalence value that exists within a threshold range of a second predictive prevalence value. Similar predictive prevalence may be identified as a function of a degree of vector similarity between a vector representing each predictive prevalence value and a vector representing another predictive prevalence value; vector similarity may be measured according to any norm for proximity and/or similarity of two vectors, including without limitation cosine similarity. As used in this disclosure a "vector" is a data structure that represents one or more a quantitative values and/or measures of predictive prevalence value 112. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes.

In an embodiment, and still referring to FIG. 1, a "cosine similarity," as used herein is a measure of similarity between two-non-zero vectors of a vector space, wherein determining the similarity includes determining the cosine of the angle between the two vectors. Cosine similarity may be computed as a function of using a dot product of the two vectors divided by the lengths of the two vectors, or the dot product of two normalized vectors. For instance, and without limitation, a cosine of 0° is 1, wherein it is less than 1 for any angle in the interval (0,π) radians. Cosine similarity may be a judgment of orientation and not magnitude, wherein two vectors with the same orientation have a cosine similarity of 1, two vectors oriented at 90° relative to each other have a similarity of 0, and two vectors diametrically opposed have a similarity of −1, independent of their magnitude. As a non-limiting example, vectors may be considered similar if parallel to one another. As a further non-limiting example, vectors may be considered dissimilar if orthogonal to one another. As a further non-limiting example, vectors may be considered uncorrelated if opposite to one another. Additionally or alternatively, degree of similarity may include any other geometric measure of distance between vectors. As a further non-limiting example, similar predictive prevalence may denote that a first well may include 8 specimens that share a similar predictive prevalence value of 0.12 for obtaining a positive result for the common cold, wherein a second well may include 20 specimens that share a similar predictive prevalence value of 0.021 likelihood for obtaining a positive result for the common cold. In an embodiment, and without limitation, computing device 104 may generate the assignment as a function of the similar predictive prevalence value. For example, and without limitation, computing device 104 may generate assignment as a function of a plurality of lab specimens that share a similar predictive prevalence value of 0.013. As a further non-limiting example, computing device 104 may generate assignment as a function of a plurality of lab specimens that share a similar predictive prevalence value of 0.21.

Still referring to FIG. 1, computing device 104 may produce a pool database as a function of assigning lab specimen to the well. As used in this disclosure a "pool database" is a database that stores feature data associated with the plurality of patients and/or individuals. Pool database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Pool database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. For example, and without limitation, pool database may store one or more feature datum entries such as patient demographics, occupations, medical records, and the like thereof. In an embodiment, and without limitation, computing device 104 may produce pool database as a function of identifying a delegated pooling strategy. As used in this disclosure a "delegated pooling strategy" is a plan and/or scheme for analyzing a plurality of lab specimens and/or analytes. For example, and without limitation, delegated pooling strategy may denote that a first well comprises 8 lab specimens, wherein a second well comprises 20 lab specimens, wherein a third well comprises 3 lab specimens. As a further non-limiting example, delegated pooling strategy may denote that a first well shares similar feature data representing an occupation of a healthcare worker, wherein a second well shares similar feature data representing an occupation of an account.

Still referring to FIG. 1, computing device 104 may be further configured to determine a deviant outcome as a function of lab specimen. As used in this disclosure a "deviant outcome" is a result and/or analysis that differs from the expected outcome and/or probabilistic outcome. For example, and without limitation, deviant outcome may denote that a lab specimen and/or group of lab specimens had a high probability of being negative for COVID-19, wherein the result and/or analysis denoted a positive result for COVID-19. As a further non-limiting example, deviant outcome may denote that a lab specimen and/or group of lab specimens had a high probability of being positive for influenza, wherein the result and/or analysis denoted a negative result for influenza. In an embodiment, and without limitation, computing device 104 may be configured to identify a retest element as a function of the deviant outcome. As used in this disclosure a "retest element" is an element of data denoting that a subsequent and/or additional analysis should be performed on the lab specimens and/or group of lab specimens located in the well. For example, and without limitation, a retest element may denote that a well containing eight lab specimens that were expected to test negative, wherein the result was positive, may need to be analyzed additionally, wherein the well may no longer be grouped and/or pooled together. As a further non-limiting example, retest element may denote that a well containing twenty lab specimens may need to be further reduced such that a difference among the predictive prevalence values is reduced to increase the probability of achieving the expected result.

Figure 2:
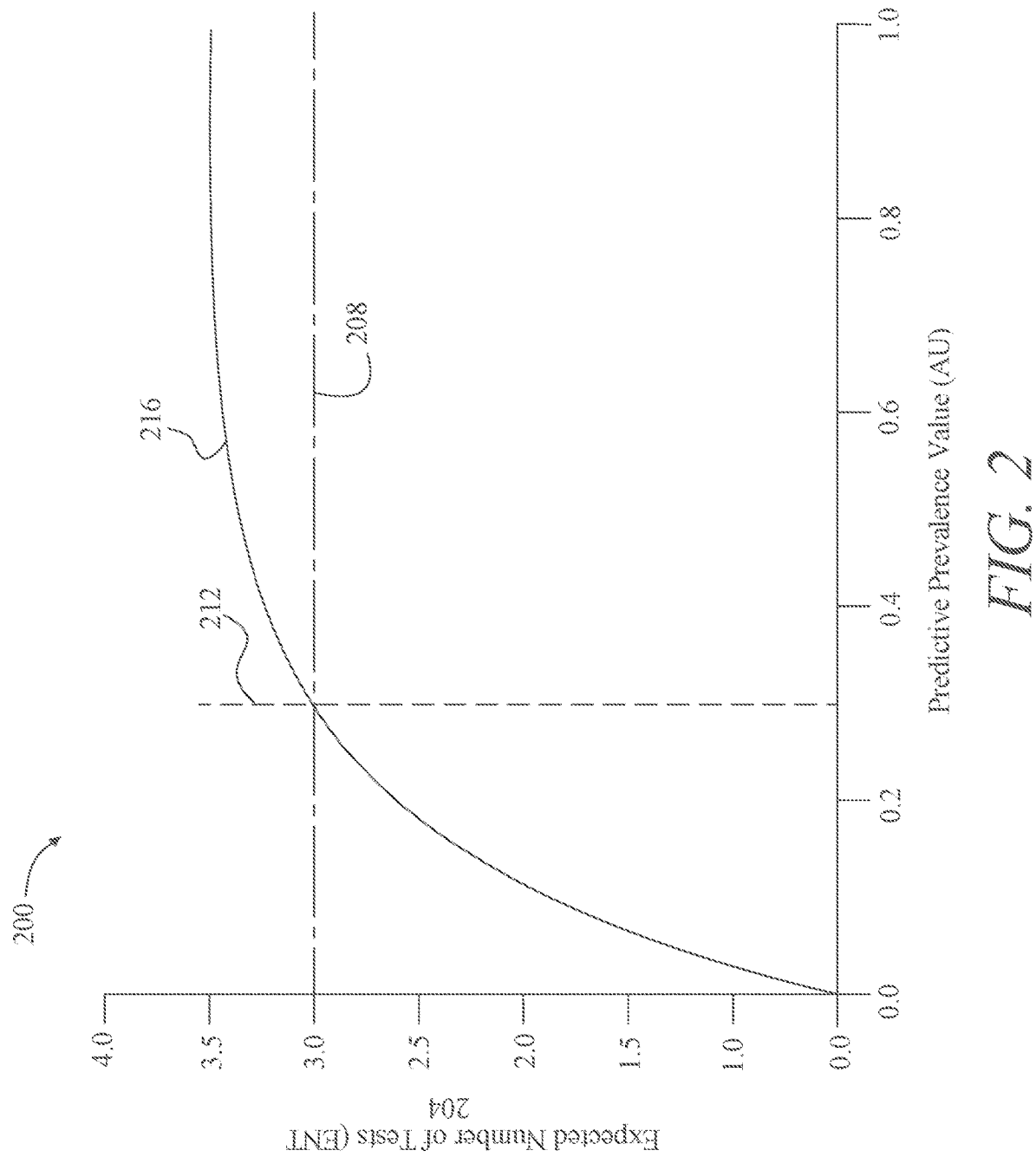
FIG. 2 is a diagrammatic representation of an exemplary embodiment of a first delegated pooling strategy.

Now referring to FIG. 2, an exemplary embodiment 200 of a first delegated pooling strategy is illustrated. In an embodiment and without limitation, an expected number of tests (ENT) 204 may be located along a y-axis, wherein predictive prevalence value is located along an x-axis. As used in this disclosure an "expected number of tests" is the number of lab specimens and/or samples to be analyzed for a given viral agent and/or bacterial infection. For example, and without limitation, expected number of tests may include a number of 3 lab specimens and/or samples to be analyzed. In an embodiment, and without limitation, first delegated pooling strategy may include a first well count 208. As used in this disclosure a "well count" is a number of lab specimens and/or analytes to be pooled to a well. For example, first well count 208 may be set to 3 samples per well. In another embodiment, and without limitation, first delegated pooling strategy may include a first pooling threshold 212. As used in this disclosure a "first pooling threshold" is a pooling threshold for a first delegated pooling strategy. For example, first pooling threshold may be a value of 0.307. In an embodiment, and without limitation, first delegated pooling strategy may include an ENT per prevalence curve 216. As used in this disclosure an "ENT per prevalence curve" is a representation denoting when lab specimens and/or analytes may be pooled and/or grouped together. For example, and without limitation, ENT 204 within first well count 208 and first pooling threshold 212 may be pooled together, wherein an ENT 204 outside of well count 208 and/or first pooling threshold 212 may not be pooled together.

Figure 3:
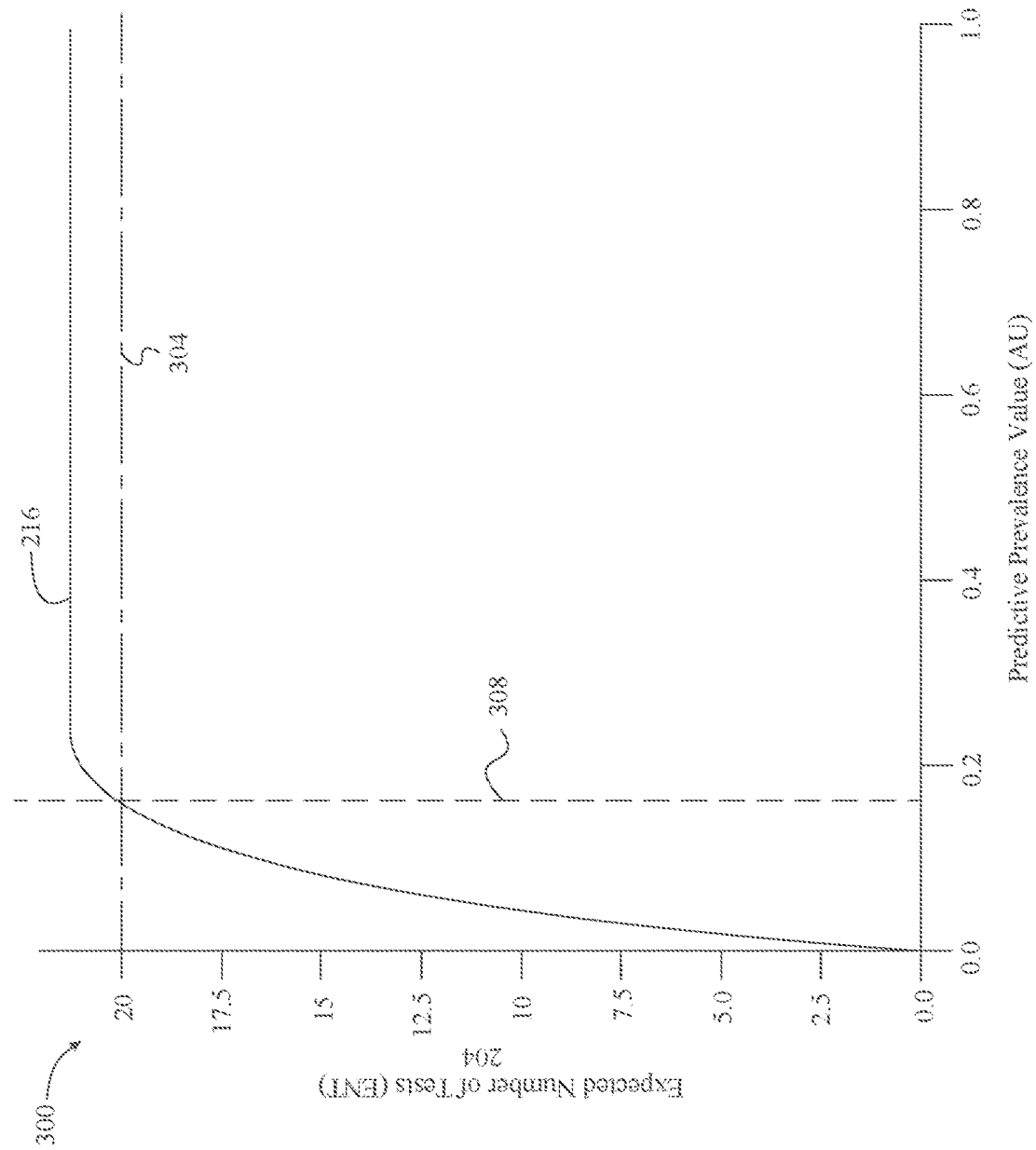
FIG. 3 is a diagrammatic representation of an exemplary embodiment of a second delegated pooling strategy.

Now referring to FIG. 3, an exemplary embodiment 300 of a second delegated pooling strategy is illustrated. In an embodiment and without limitation, expected number of tests (ENT) 204 may be located along a y-axis, wherein predictive prevalence value is located along an x-axis, and wherein an expected number of tests (ENT) 204 is described above in detail, in reference to FIG. 2. In an embodiment, and without limitation, second delegated pooling strategy may include a second well count 304, wherein a well count is described above, in reference to FIG. 2. For example, second well count 304 may be set to 20 samples per well. In another embodiment, and without limitation, second delegated pooling strategy may include a second pooling threshold 308. As used in this disclosure a "second pooling threshold" is a pooling threshold for a second delegated pooling strategy. For example, second pooling threshold may be a value of 0.139. In an embodiment, and without limitation, second delegated pooling strategy may include an ENT per prevalence curve 216. As used in this disclosure an "ENT per prevalence curve" is a mathematical function that denotes a prevalence and/or ENT that may be pooled together. For example, and without limitation, ENT 204 within well count 208 and first pooling threshold 212 may be pooled together, wherein an ENT 204 outside of second well count 308 and/or second pooling threshold 308 may not be pooled together.

Figure 4:
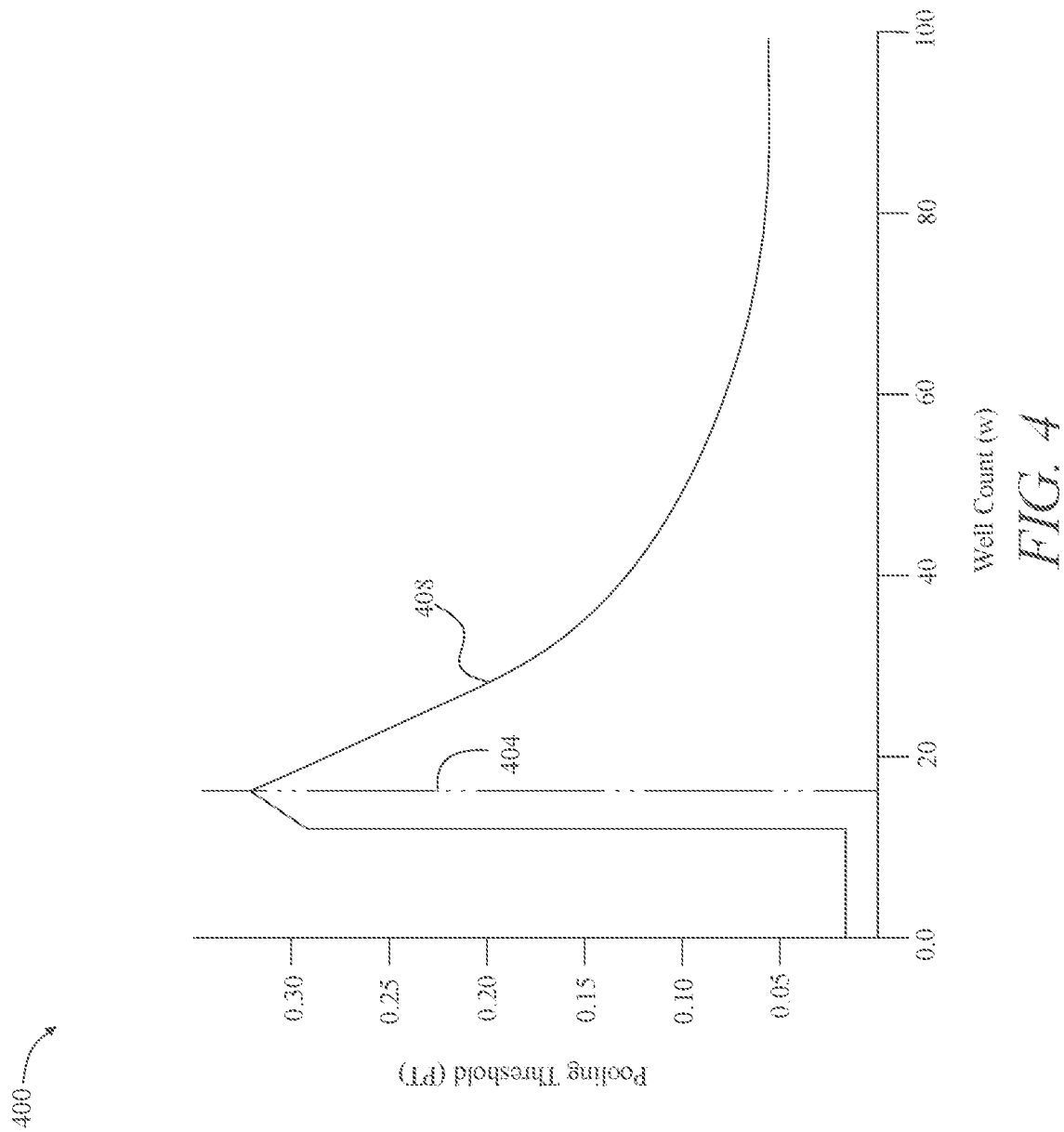
FIG. 4 is a diagrammatic representation of an exemplary embodiment of a pooling threshold.

Now referring to FIG. 4, an exemplary embodiment 400 of pooling threshold 128 is illustrated. In an embodiment and without limitation, pooling threshold 128 may include a maximum pooling threshold 404. As used in this disclosure a "maximum pooling threshold" is a pooling threshold that may denote that pooling and/or grouping is no longer effective. For example, and without limitation, maximum pooling threshold 404 may denote that efficiency of pooling and/or grouping will decrease and/or be eliminated when predictive prevalence value is greater than 0.307. As a further non-limiting example, maximum pooling threshold 404 may denote that an efficiency of pooling and/or grouping will exist at predictive prevalence values of less than 0.297. In an embodiment, and without limitation, pooling threshold 128 may denote a threshold curve 408. As used in this disclosure a "threshold curve" is a mathematical function that denotes when pooling and/or grouping is efficient as a function of the well count. For example, and without limitation threshold count 408 may denote that for a 5 well count the predictive prevalence value must be below 0.301 to be efficient.

Figure 5:
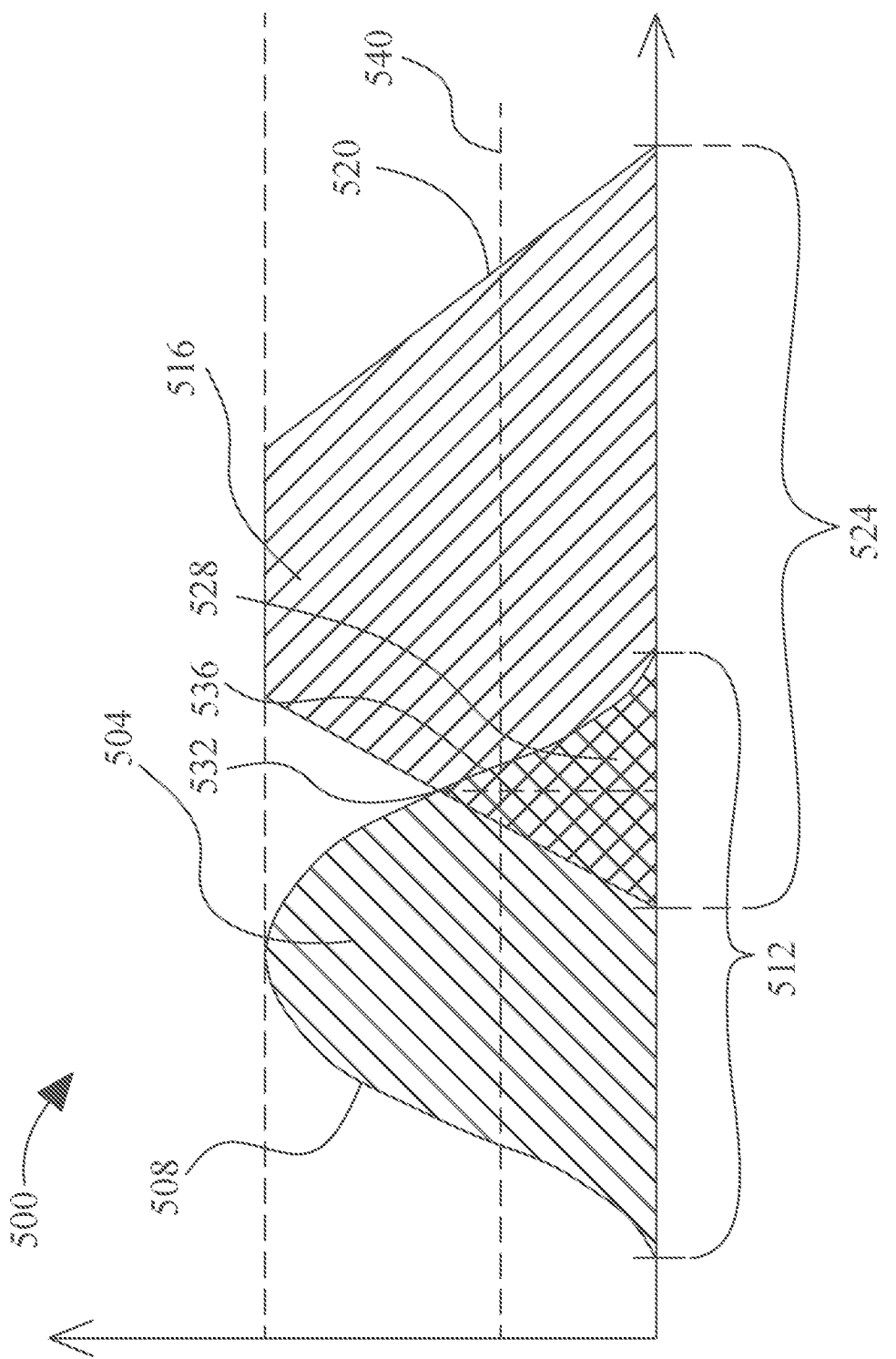
FIG. 5 is a block diagram illustrating exemplary embodiments of fuzzy sets.

Now referring to FIG. 5, an exemplary embodiment of fuzzy set comparison 500 is illustrated. A first fuzzy set 504 may be represented, without limitation, according to a first membership function 508 representing a probability that an input falling on a first range of values 512 is a member of the first fuzzy set 504, where the first membership function 508 has values on a range of probabilities such as without limitation the interval [0,1], and an area beneath the first membership function 508 may represent a set of values within first fuzzy set 504. Although first range of values 512 is illustrated for clarity in this exemplary depiction as a range on a single number line or axis, first range of values 512 may be defined on two or more dimensions, representing, for instance, a Cartesian product between a plurality of ranges, curves, axes, spaces, dimensions, or the like. First membership function 508 may include any suitable function mapping first range 512 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 504 may represent any value or combination of values as described above, including predictive prevalence value, probabilistic outcome, any resource datum, any niche datum, and/or any combination of the above. A second fuzzy set 516, which may represent any value which may be represented by first fuzzy set 504, may be defined by a second membership function 520 on a second range 524; second range 524 may be identical and/or overlap with first range 512 and/or may be combined with first range via Cartesian product or the like to generate a mapping permitting evaluation overlap of first fuzzy set 504 and second fuzzy set 516. Where first fuzzy set 504 and second fuzzy set 516 have a region 228 that overlaps, first membership function 508 and second membership function 520 may intersect at a point 532 representing a probability, as defined on probability interval, of a match between first fuzzy set 504 and second fuzzy set 516. Alternatively or additionally, a single value of first and/or second fuzzy set may be located at a locus 536 on first range 512 and/or second range 524, where a probability of membership may be taken by evaluation of first membership function 508 and/or second membership function 520 at that range point. A probability at 528 and/or 532 may be compared to a threshold 540 to determine whether a positive match is indicated. Threshold 540 may, in a non-limiting example, represent a degree of match between first fuzzy set 504 and second fuzzy set 516, and/or single values therein with each other or with either set, which is sufficient for purposes of the matching process; for instance, threshold may indicate a sufficient degree of overlap between probabilistic outcomes and/or predictive prevalence values 112 for combination to occur as described above. There may be multiple thresholds; for instance, a second threshold may indicate a sufficient match for purposes of pooling threshold 128 as described in this disclosure. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if two predictive prevalence values 112 have fuzzy sets matching a probabilistic outcome fuzzy set by having a degree of overlap exceeding a threshold, computing device 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple predictive prevalence values 112 may be presented to a user in order of ranking.

Figure 6:
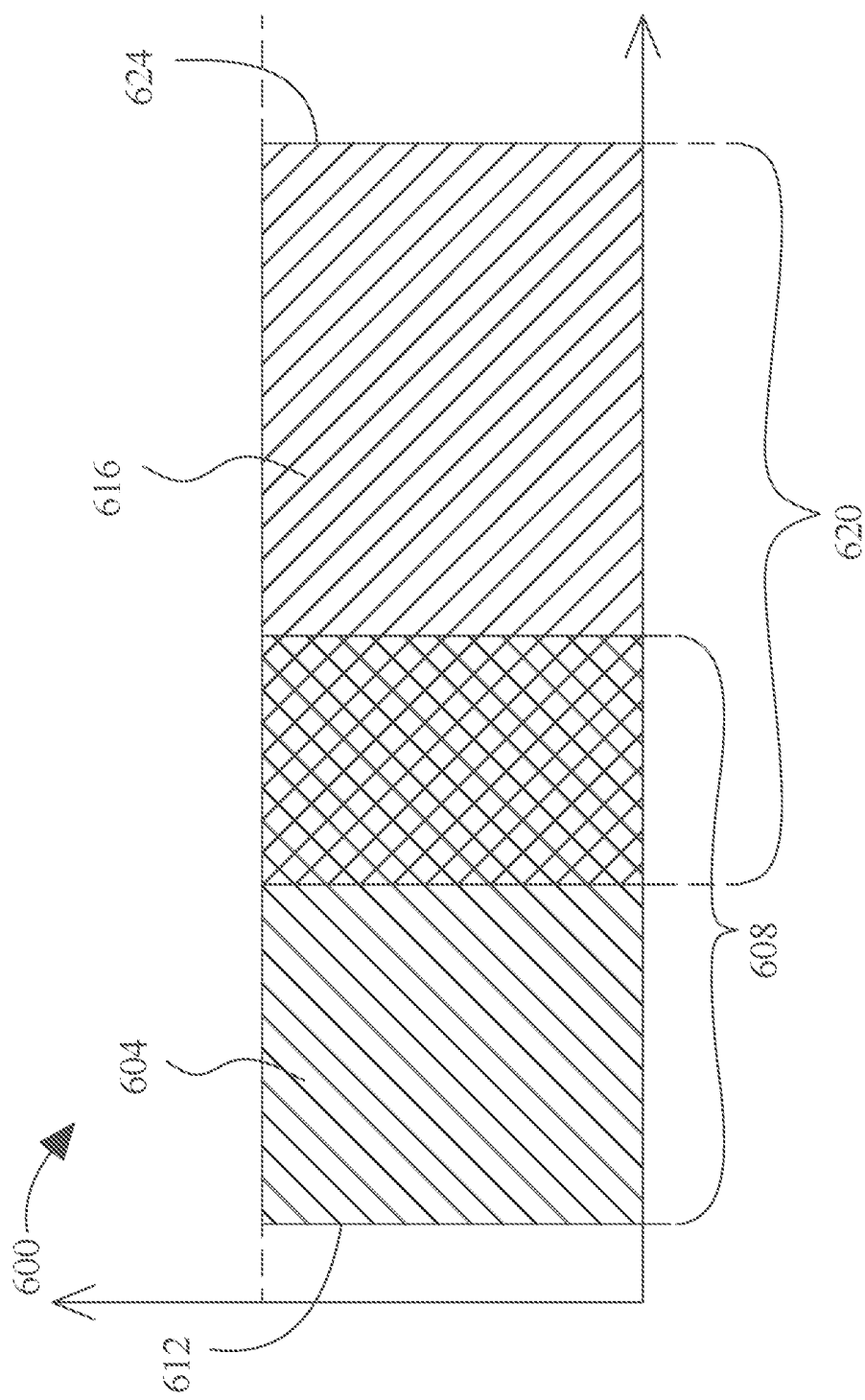
FIG. 6 is a block diagram illustrating exemplary embodiments of bivalent sets.

Referring now to FIG. 6, an exemplary embodiment of comparison of bivalent sets on ranges is illustrated. A first bivalent set 604 may be defined on a first range 608, which may have any form suitable for use as a first range 512 for a fuzzy set as described above. In an embodiment, first bivalent set 604 may be defined according to a first characteristic function 612, which may include, without limitation, a step function having output values on a probability interval such as [0,1] or the like; step function may have an output representing 100% or probability of 1 for values falling on first range 608 and zero or a representation of zero probability for values not on first range 608. A second bivalent set 616 may be defined on a second range 620, which may include any range suitable for use as first range 608. Second bivalent set may be defined by a second characteristic function 624, which may include any function suitable for use as first characteristic function 612. In an embodiment a match between first bivalent set 608 and second bivalent set 620 may be established where first range 608 intersects second range 620, and/or where first characteristic function 612 and second characteristic function 624 share at least one point in first range 308 and second range 616 at which both first characteristic function 612 and second characteristic function 624 are non-zero.

Figure 7:
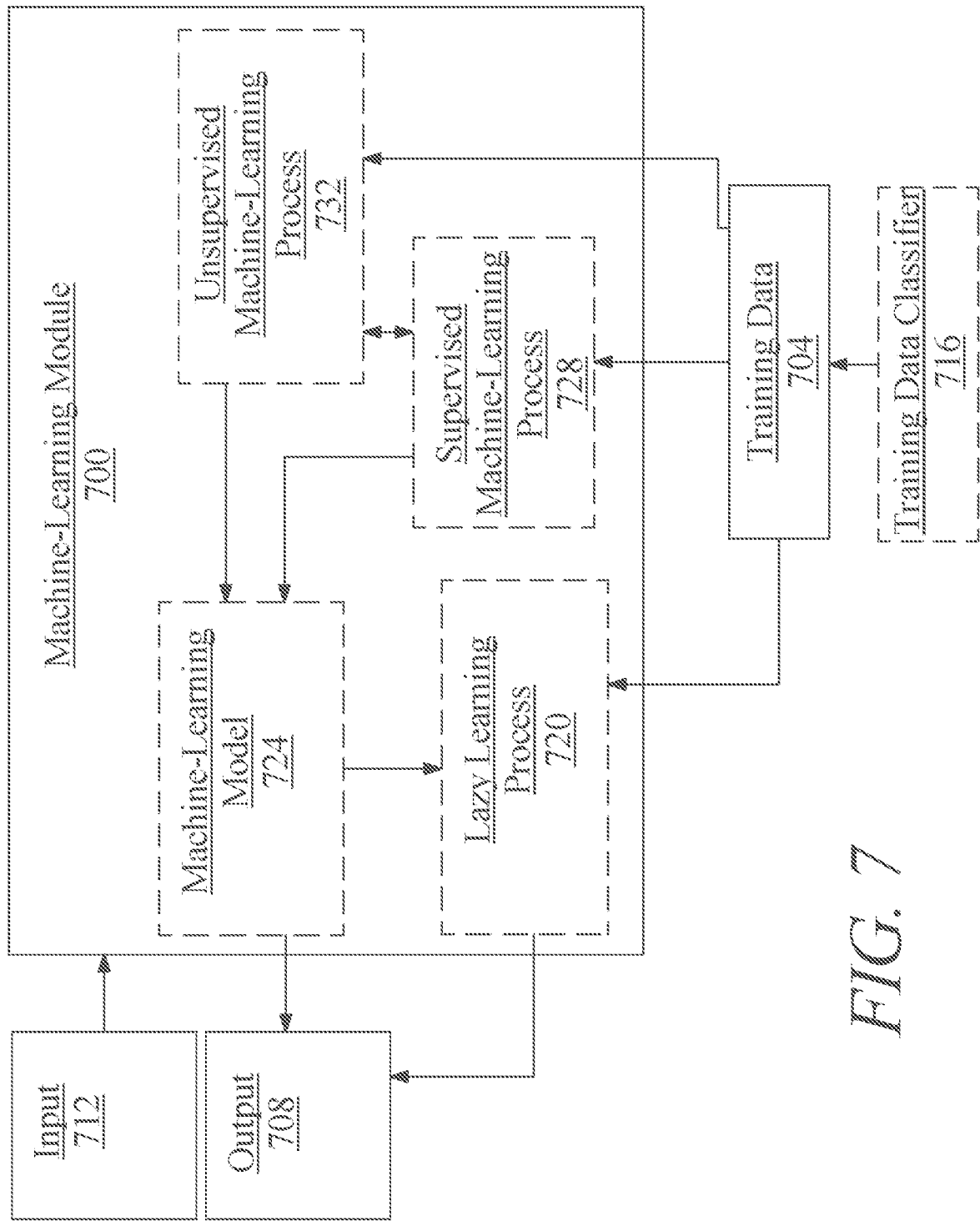
FIG. 7 is a block diagram illustrating an exemplary embodiment of a machine-learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative, at least a feature datum input may correlate to a predictive prevalence value output.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include feature datum as described above as inputs, predictive prevalence values as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 8:
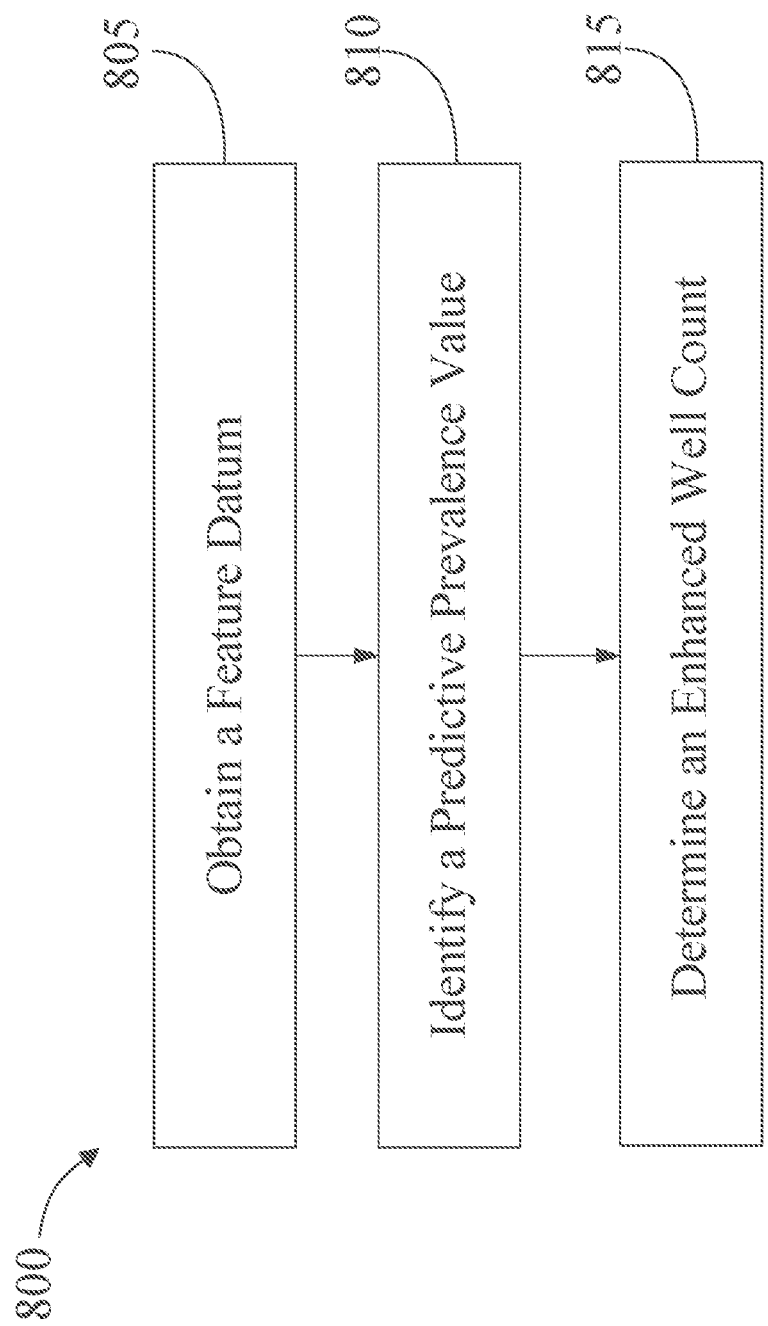
FIG. 8 is a flow diagram illustrating an exemplary embodiment of a method for smart pooling.

Now referring to FIG. 8, an exemplary embodiment 800 of a method for smart pooling is illustrated. At step 805, a computing device 104 obtains a feature datum 108. Computing device 104 includes any of the computing device 104 as described above, in reference to FIGS. 1-7. Feature datum 108 includes any of the feature datum 108 as described above, in reference to FIGS. 1-7.

Still referring to FIG. 8, at step 810, computing device 104 identifies a predictive prevalence value 112. Predictive prevalence value 112 includes any of the predictive prevalence value 112 as described above, in reference to FIGS. 1-7. Computing device 104 identifies predictive prevalence value 112 as a function of receiving a predictive training set 116 correlating feature datum 108 with a probabilistic outcome. Predictive training set 116 includes any of the predictive training set 116 as described above, in reference to FIGS. 1-7. Probabilistic outcome includes any of the probabilistic outcome as described above, in reference to FIGS. 1-7. Predictive prevalence value 112 is identified as a function of training a predictive machine-learning model 120 as a function of predictive training set 116. Predictive machine-learning model 120 includes any of the predictive machine-learning model 120 as described above, in reference to FIGS. 1-7. Predictive prevalence value 112 is identified as a function of predictive machine-learning model 120 and feature datum 108.

Still referring to FIG. 8, at step 815, computing device 104 determines an enhanced well count 124. Enhanced well count 124 includes any of the enhanced well count 124 as described above, in reference to FIGS. 1-7. Enhanced well count 124 is determined as a function of generating a pooling threshold 128. Pooling threshold 128 includes any of the pooling threshold 128 as described above, in reference to FIGS. 1-7. Enhanced well count 124 is determined as a function of pooling threshold 124 and predictive prevalence value 112.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
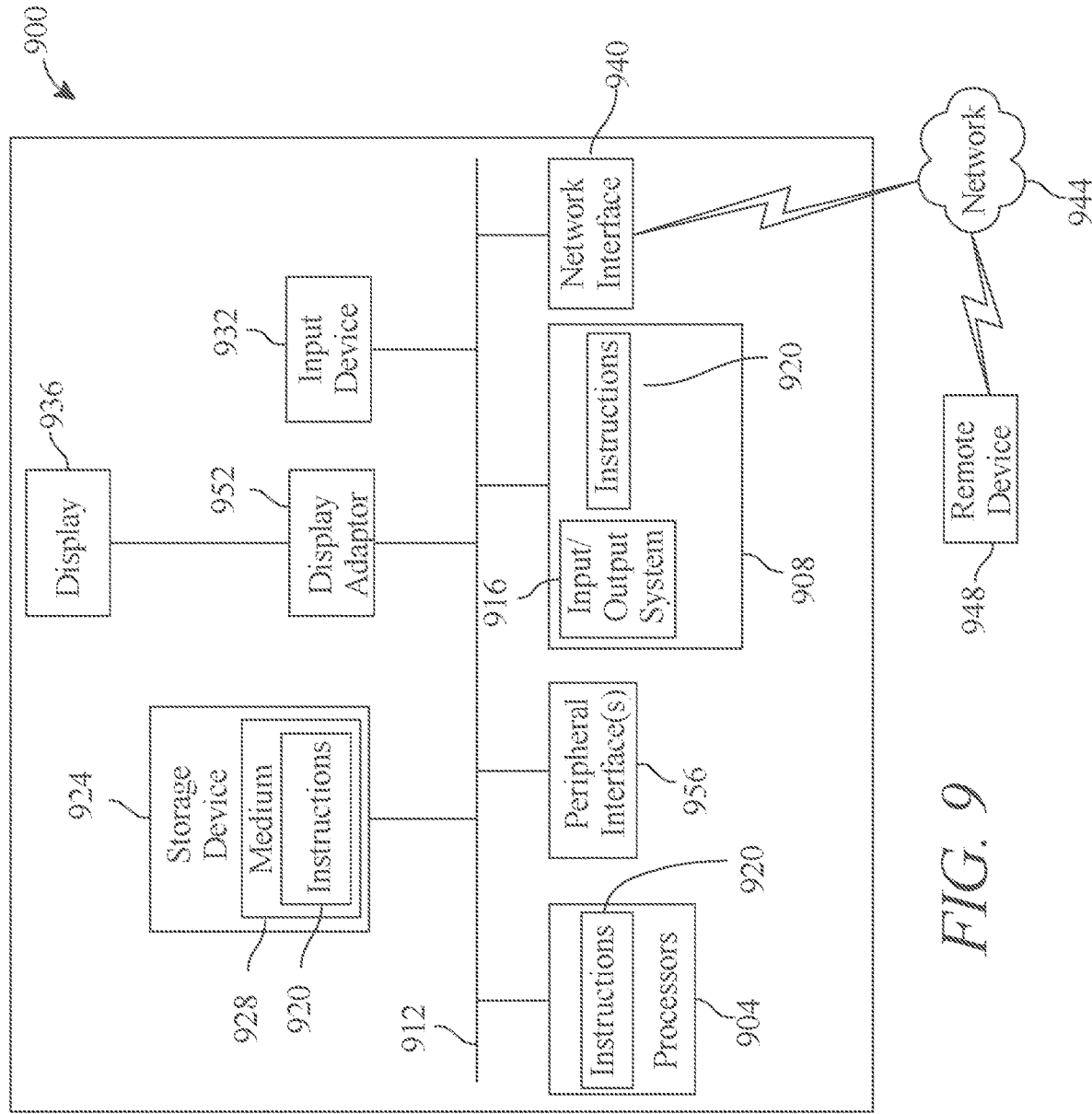
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for smart pooling, the system comprising a computing device, wherein the computing device is configured to:
   obtain a feature datum;
   identify a predictive prevalence value as a function of the feature datum, wherein identifying the predictive prevalence value further comprises:
   receiving a predictive training set correlating the feature datum with a probabilistic outcome, wherein the probabilistic outcome includes a contagion factor;
   training a predictive machine-learning model as a function of the predictive training set; and identifying the predictive prevalence value as a function of the trained predictive machine-learning model and the feature datum; and
determine an enhanced well count, wherein determining the enhanced well count further comprises:
generating a pooling threshold; and
determining the enhanced well count as a function of the pooling threshold and the predictive prevalence value.

2. The system of claim 1, wherein obtaining the feature datum further comprises identifying a clinical element and obtaining the feature datum as a function of the clinical element.

3. The system of claim 1, wherein obtaining the feature datum further comprises receiving a medical input and obtaining the feature datum as a function of the medical input.

4. The system of claim 1, wherein identifying the predictive prevalence value further comprises determining a probabilistic distribution and identifying the predictive prevalence value as a function of the probabilistic distribution.

5. The system of claim 1, wherein generating the pooling threshold further comprises:
receiving a probability limiter; and
generating the pooling threshold as a function of the probability limiter.

6. The system of claim 1, wherein the computing device is further configured to:
receive a lab specimen associated with the feature datum;
generate an assignment of the lab specimen to a well as a function of the enhanced well count; and
produce a pool database as a function of assigning the lab specimen to the well.

7. The system of claim 6, wherein generating the assignment further comprises:
receiving a grouping element; and
generating the assignment the lab specimen as a function of the grouping element and a grouping machine-learning model.

8. The system of claim 6, wherein generating the assignment further comprises:
identifying a similar predictive prevalence; and
generating the assignment as a function of the similar predictive prevalence.

9. The system of claim 6, wherein producing the pool database further comprises identifying a delegated pooling strategy and producing the pool database as a function of the delegated pooling strategy.

10. The system of claim 6, wherein the computing device is further configured to:
determine a deviant outcome as a function of the lab specimen; and
identify a retest element as a function of the deviant outcome.

11. A method for smart pooling, the method comprising:
obtaining, by a computing device, a feature datum;
identifying, by the computing device, a predictive prevalence value as a function of the feature datum, wherein identifying the predictive prevalence value further comprises:
receiving a predictive training set correlating the feature datum with a probabilistic outcome, wherein the probabilistic outcome includes a contagion factor;
training a predictive machine-learning model as a function of the predictive training set; and
identifying the predictive prevalence value as a function of the trained predictive machine-learning model and the feature datum; and
determining, by the computing device, an enhanced well count, wherein determining the enhanced well count further comprises:
generating a pooling threshold; and
determining the enhanced well count as a function of the pooling threshold and the predictive prevalence value.

12. The method of claim 11, wherein obtaining the feature datum further comprises identifying a clinical element and obtaining the feature datum as a function of the clinical element.

13. The method of claim 11, wherein obtaining the feature datum further comprises receiving a medical input and obtaining the feature datum as a function of the medical input.

14. The method of claim 11, wherein identifying the predictive prevalence value further comprises determining a probabilistic distribution and identifying the predictive prevalence value as a function of the probabilistic distribution.

15. The method of claim 11, wherein generating the pooling threshold further comprises:
receiving a probability limiter; and
generating the pooling threshold as a function of the probability limiter.

16. The method of claim 11, further comprising:
receiving a lab specimen associated with the feature datum;
generating an assignment of the lab specimen to a well as a function of the enhanced well count; and
producing a pool database as a function of assigning the lab specimen to the well.

17. The method of claim 16, wherein generating the assignment further comprises:
receiving a grouping element; and
generating the assignment the lab specimen as a function of the grouping element and a grouping machine-learning model.

18. The method of claim 16, wherein generating the assignment further comprises:
identifying a similar predictive prevalence;
generating the assignment as a function of the similar predictive prevalence.

19. The method of claim 16, wherein producing the pool database further comprises identifying a delegated pooling strategy and producing the pool database as a function of the delegated pooling strategy.

20. The method of claim 16, further comprising:
determining a deviant outcome as a function of the lab specimen; and
identifying a retest element as a function of the deviant outcome.

* * * * *